United States Patent [19]

Cohen

[11] Patent Number: 5,117,306
[45] Date of Patent: May 26, 1992

[54] DIFFRACTION BIFOCAL WITH ADJUSTED CHROMATICITY

[76] Inventor: Allen L. Cohen, 10010 Walsham Ct., Richmond, Va. 23233

[21] Appl. No.: 553,336

[22] Filed: Jul. 17, 1990

[51] Int. Cl.$^5$ .............. G02C 7/04; G02B 27/44; G02B 3/10; A61F 2/16
[52] U.S. Cl. .................... 359/565; 351/161; 351/168; 623/6; 359/569; 359/721; 359/743
[58] Field of Search ............ 623/6; 351/161, 168, 351/172; 350/437, 452, 162.16, 162.20, 162.22; 359/565, 569, 571, 721, 742, 743

[56] References Cited

U.S. PATENT DOCUMENTS

| | | | |
|---|---|---|---|
| 3,004,470 | 10/1961 | Rühle | 359/721 |
| 3,797,915 | 3/1974 | Land | 359/742 |
| 4,210,391 | 7/1980 | Cohen | 351/161 |
| 4,336,989 | 6/1982 | Matsumura et al. | 354/200 |
| 4,655,565 | 4/1987 | Freeman | 351/161 X |
| 4,673,406 | 6/1987 | Schlegel | 623/6 |
| 4,828,558 | 5/1989 | Kelman | 623/6 |
| 4,881,805 | 11/1989 | Cohen | 351/161 |
| 4,890,913 | 1/1990 | DeCarle | 351/161 |
| 5,017,000 | 5/1991 | Cohen | 351/161 |

FOREIGN PATENT DOCUMENTS 802918 10/1958 United Kingdom.
1154360 6/1969 United Kingdom.

OTHER PUBLICATIONS

H. Dammann, "Color Separation Gratings", Applied Optics, vol. 17, No. 15, Aug. 1978, pp. 2273-2279.
A. I. Tudorovskii, "An Objective with a Phase Plate", Optics and Spectroscopy, Feb. 1959, vol. VI, No. 2, pp. 126-133.
V. V. Vereshchagin and A. I. Lopatin, "Chromatic Properties of Profiled Zone Plates", Opt. Spectrosc. (USSR), vol. 46, No. 5, May 1979 (translation by Opt. Soc. of Amer., 1979), pp. 563-566.
V. V. Vereshchagin and A. I. Lopatin, "Chromatic Properties of Profiled Zone Plates; Cont'd", Opt. Spectrosc. (USSR), vol. 47, No. 1, Jul. 1979 (translation by Opt. Soc. of Amer., 1980), pp. 89-92.
Jordan et al., "Kinoform Lenses", Applied Optics, vol. 9, No. 8, Aug. 1970, pp. 1883-1887.
Kenro Miyamoto, "The Phase Fresnel Lens", Journal of the Optical Society of America, vol. 51, No. 1, No. 1, Jan., 1961, pp. 17-20.

Primary Examiner—Bruce Y. Arnold
Assistant Examiner—David R. Parsons

[57] ABSTRACT

A diffraction bifocal lens or lens system, comprising two profiled surfaces or interfaces or a linear combination thereof, wherein one profile provides for the bifocality of the lens and the other profile compensates for chromatic aberration. These lenses or lens systems exhibit two focal points, one which exhibits positive chromatic aberration and the other which exhibits negative chromatic aberration.

24 Claims, 6 Drawing Sheets $$r_K = \sqrt{K\lambda d} \quad R_K = \sqrt{K\lambda D}$$

$$F_{far} = m/d - M/D$$

$$F_{near} = (m+1)/d - M/D$$

DIFFRACTION BIFOCAL WITH ADJUSTED CHROMATICITY

PRIOR ART TO THE INVENTION

Diffractive optical lenses comprise a plurality of annular concentric zones spaced according to the formula $R_k = \sqrt{kD\lambda}$, with $k=1,2,3,\ldots$, where $k$ is a zone, $D$ is the primary focal length, $\lambda$ is the design wavelength, and $R_k$ is the zone radius. A basic phase shifting profile, characteristic of each particular lens, is repeated within each zone. This profile determines the optical properties of the lens.

Monofocal diffractive lenses have been described by Jordan, et. al. (Applied Optics, Vol. 9, No. 8, August 1970). These lenses have profiles designed to diffract light into a single order M (see FIG. 1) defined by the focal point $f_M = D/M$, with D the primary focal length of the monofocal and $M=0, \pm 1, \pm 2, \ldots$. The power $F_M$ of the lens, with respect to the design wavelength $\lambda$, is given by $F_M = M/D$. Different wavelengths, designated for example as $\lambda_r$ and $\lambda_b$, will have different powers (see FIG. 2) which may be designated as $F_r$ and $F_b$ respectively. In particular, if we choose $\lambda_r > \lambda > \lambda_b$, then we will have $F_r > F_M > F_b$ for the case when $M>0$, while we will have $F_r < F_M < F_b$ for the case when $M<0$.

In order to convey a sense of the magnitude of this spread in focal powers, we usually specify the longitudinal chromatic aberration (long. c.a.) of the lens. Given a specific set of values $\lambda_r > \lambda > \lambda_b$ (typically we will choose $\lambda_r = 656$ nm, $\lambda = 555$ nm, and $\lambda_b = 486$ nm), we have for the long. c.a. $L_M$;

$$L_M = F_r - F_b = \omega M/D \text{ with } \omega = (\lambda_r - \lambda_b)/\lambda.$$

Bifocal diffractive lenses are described by Cohen (U.S. Pat. No. 4,340,283), and have profiles designed to diffract light into two separate and distinct orders. In ophthalmic lenses the more positive order is used for near vision while the less positive order is used for far vision. For this reason it is convenient to label the powers associated with the more positive and less positive orders, $F_{near}$ and $F_{far}$ respectively (see FIG. 3). Similarly, we may label the long. c.a. for these orders as $L_{near}$ and $L_{far}$. For bifocals, we can define the bifocal power (A), as well as the bifocal long. c.a. (B) according to the equations $$A = F_{near} - F_{far} \text{ and } B = L_{near} - L_{far}.$$

The prior art (U.K. Pat. No. 802,918 issued to Jeffree), has shown bifocals that diffract light to the +1st and −1st orders defined by the focal points $f_{\pm 1} = \pm d$, with d the primary focal length of the bifocal. If we want these lenses to have the bifocal power A, we must choose $d = \frac{1}{2}A$ and then $$B = \omega A \text{ with } L_{near} = \omega A/2 \text{ and } L_{far} = \omega A/2.$$

The prior art (U.S. Pat. No. 4,340,283 issued to Cohen), has also disclosed bifocals that use the mth and (m+1)th orders defined by the focal points $f_m = d/m$ and $f_{m+1} = d/(M+1)$, where d is again taken as the primary focal length of the bifocal and $m=0, \pm 1, \pm 2, \ldots$. If we want these lenses to have the bifocal power A, we must choose $d = 1/A$ and then $$B = \omega A \text{ with } L_{near} = \omega(m+1)A \text{ and } L_{far} = \omega MA.$$

In the particular case of a 0th and +1st order bifocal (i.e. $m=0$) we have $$B = \omega A \text{ with } L_{near} = \omega A \text{ and } L_{far} = 0,$$

and in the case of a 0th and −1st order bifocal (i.e. $m=-1$) we have $$B = \omega A \text{ with } L_{near} = 0 \text{ and } L_{far} = -\omega A.$$

SUMMARY OF THE INVENTION

The crystalline lens of the human eye exhibits a significant amount of negative chromatic aberration. The chromatic aberration inherent in a diffractive lens, will add linearly to the chromatic aberration of the eye of the user. Thus, if a lens has negative chromatic aberration, it will increase the total chromatic aberration of the lens eye system. However, if a lens has positive chromatic aberration, it will decrease the total chromatic aberration of the lens eye system. Because of this, the human visual system will tolerate more positive chromatic aberration than negative chromatic aberration.

However, it is desirable that a bifocal lens present to the eye two images of equal clarity. If both images have chromatic aberration, then we will obtain two images of equal clarity when one of the images has positive chromatic aberration, and the other image has negative chromatic aberration of a lesser magnitude.

For any given bifocal power A, a diffraction bifocal will exhibit a corresponding bifocal long. c.a. $B = \omega A$. To provide images of equal clarity we must divide the chromatic aberration between the two focal points according to $$L_{near} = \alpha \omega A \text{ and } L_{far} = (\alpha - 1)\omega A \text{ with } 0 < \alpha < 1.0.$$

However, there are no prior art bifocal diffractive lenses that can balance the chromatic aberrations between their two focal points by varying $\alpha$ in this arbitrary manner. For the 0th/+1st order bifocals of the prior art we have $\alpha = +1.0$ and for the 0th/−1st order bifocals of the prior art we have $\alpha = -1.0$. Finally, in the case of the +1st/−1st order bifocals of the prior art we are limited to the precisely equal split of chromatic aberration given by $\alpha = 0.5$. No prior art diffraction bifocals provide any other split of chromatic aberration between their two bifocal images.

But, according to this invention, if we combine a monofocal diffraction lens with a bifocal diffraction lens according to the formula $(m+1)/d > M/D > m/d$, then the resulting lens will show $$L_{near} = \alpha \omega A \text{ and } L_{far} = (\alpha - 1)\omega A$$

where $\alpha$ can take on any value subject only to the constraint $$\alpha = m + 1 - (Md/D) \text{ or } 0 < \alpha < 1.$$

In the case where $\alpha = 0.5$ this invention provides for a lens that is much easier to manufacture than the +1st/−1st order bifocals of the prior art which also exhibit this particular split of chromatic aberration.

In the case where $0.5 < \alpha < 1.0$ this invention provides for a lens that can balance the two images to be of equal clarity as perceived by the eye. No bifocals of the prior art exhibit this split of chromatic aberration.

In the case where $0 < \alpha < 0.5$ this invention provides for a lens with a balanced but near bias. No bifocals of the prior art exhibit this split of chromatic aberration.

Specifically, this invention comprises an optical lens or lens system with two diffractive surfaces or interfaces or a linear combination thereof. One profiled surface or interface, may be designed to diffract light to two adjacent non negative focal orders m and (m+1), while the other surface would then be designed to diffract light to the negative focal order $-M$. The two optical surfaces would be aligned so that their optical axes are coincident, and such that the focal orders of the two diffractive surfaces obey the relationship $(m+1)/d < M/D < m/d$.

Alternatively, the bifocal interface may be designed to diffract light to two adjacent non positive focal orders and the monofocal interface may be designed to diffract light to a positive focal order.

In many embodiments of this invention, the bifocal interface may be incorporated by linear superposition, into the monofocal interface to form a single composite diffractive interface according to this invention.

BRIEF DESCRIPTION OF THE DRAWINGS

FIG. 6b shows a cross-sectional blow-up view of a portion of the lens of FIG. 6a.

DESCRIPTION OF THE PREFERRED EMBODIMENTS

Figure 1:
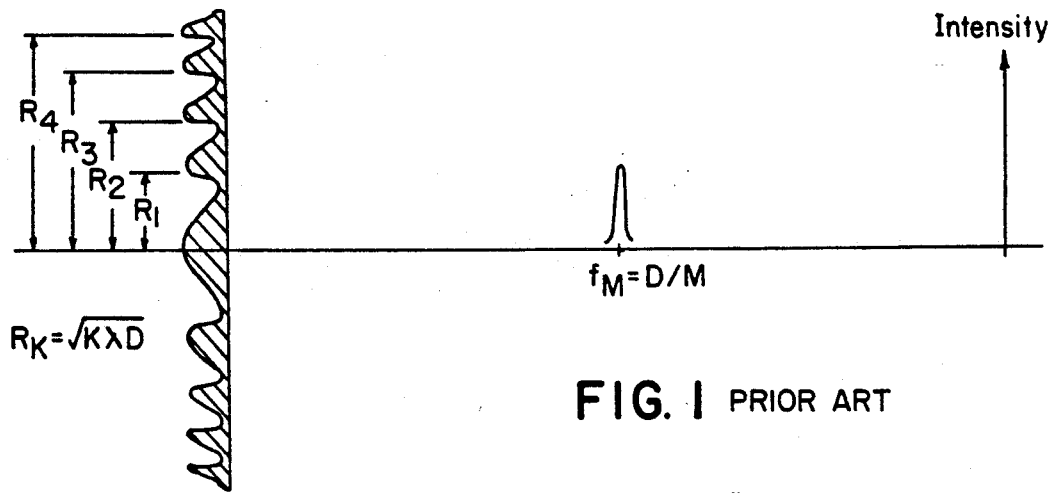
FIG. 1 shows a cross-sectional view of a prior art monofocal diffraction lens.
Figure 2:
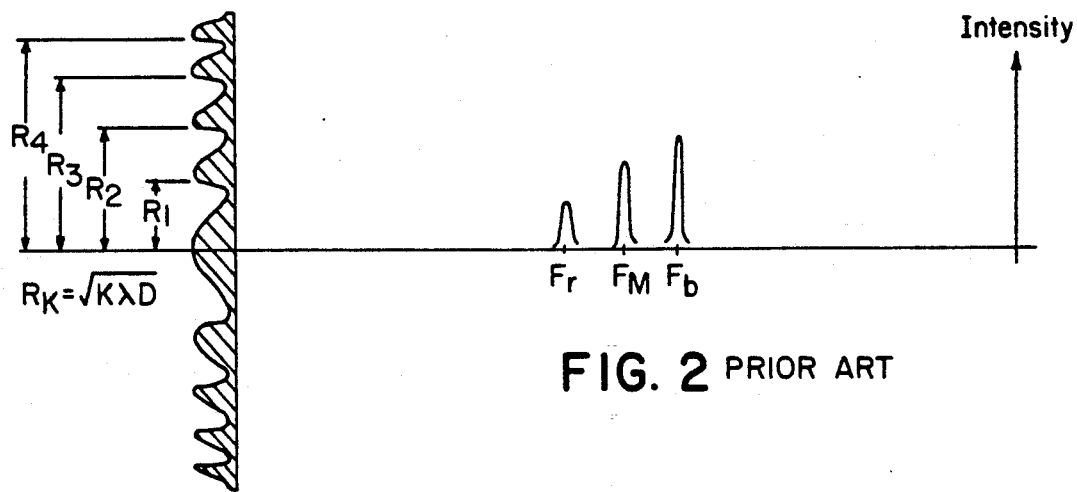
FIG. 2 shows a cross-sectional view of a prior art monofocal diffraction lens and its associated chromatic aberration.
Figure 3:
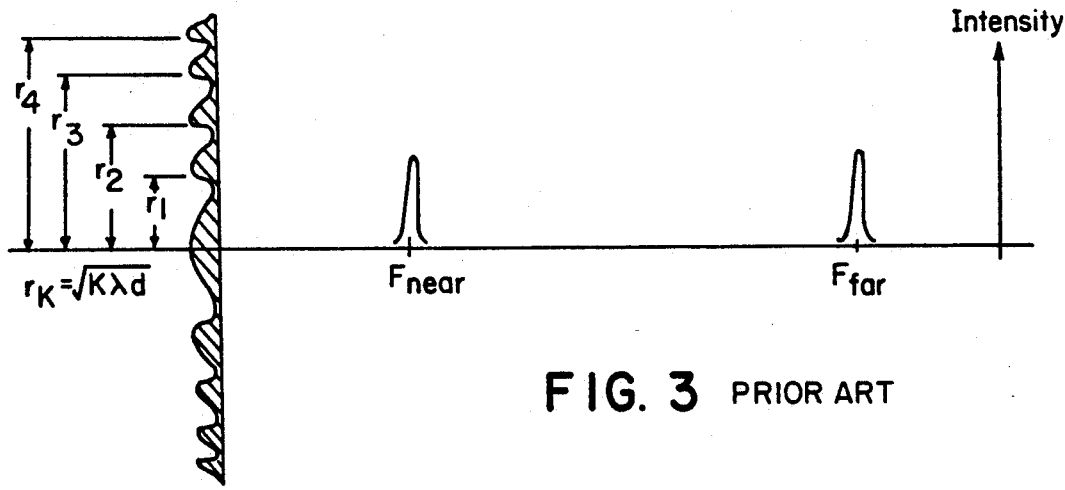
FIG. 3 shows a cross-sectional view of a portion of a prior art bifocal diffraction lens.
Figure 4:
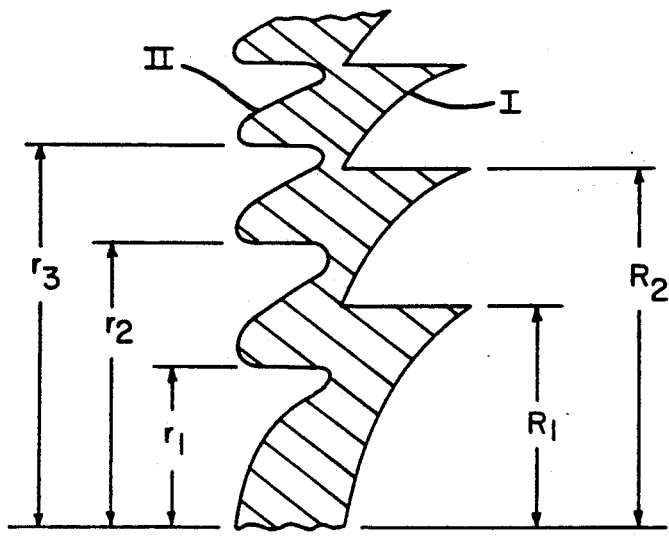
FIG. 4 shows a cross-sectional view of one embodiment of a bifocal diffraction lens according to the invention.

In FIG. 4 we have a cross-sectional view of a portion of one lens embodiment according to the invention. In this embodiment, surface I determines a $-Mth$ order monofocal where we have $M > 0$, and the annular radii $R_k$ are specified by the formula $R_k = \sqrt{K\lambda D}$. We also have in this embodiment, surface II determining a mth/(m+1)th order bifocal where $m \geq 0$, where the annular radii $r_k$ are specified by the formula $r_k = \sqrt{K\lambda d}$, and $$(m+1)/d > M/D > (m+\tfrac{1}{2})/d$$

$$L_{near} = \beta\omega A \text{ and } L_{far} = (\beta - 1)\omega A,$$

where $\beta = m + 1 - Md/D$ and $0 < \beta < \tfrac{1}{2}$. Thus, in this case the negative chromatic aberration $L_{far}$, is of a greater magnitude than the positive chromatic aberration $L_{near}$.

Figure 5:
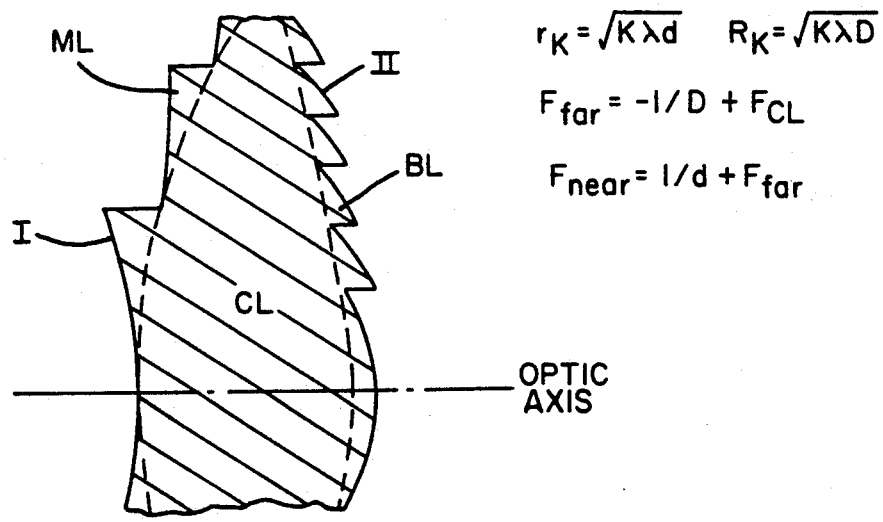
FIG. 5 shows a cross-sectional view of a portion of another embodiment of a bifocal diffraction lens according to the invention.

In FIG. 5 we have a cross-sectional view of a portion of another lens according to the invention. In the embodiment of FIG. 5, surface I determines a −1st order monofocal comprising echelettes ML, and surface II determines a 0th/+1st order bifocal comprising echelettes BL. Furthermore, in this embodiment the echelettes ML and BL are impressed upon a carrier lens CL. The carrier lens may be used to provide additional power and/or prism.

Again the bounding annular radii $R_k$ and $r_k$ of the echelettes of surface I and surface II respectively, of the embodiment of FIG. 5, are determined according to the formulae $R_k = \sqrt{k\lambda D}$ and $r_k = \sqrt{k\lambda d}$. Finally, in this particular embodiment we have, $\tfrac{1}{2}d > 1/D > 0$, giving us;

$$L_{near} = \beta\omega A \text{ and } L_{far} = (\beta - 1)\omega A,$$

where $\beta = 1 - d/D$ and $\tfrac{1}{2} < \beta < 1$.

Thus, in this case the negative chromatic aberration $L_{far}$, is of a lesser magnitude than the positive chromatic aberration $L_{near}$.

Figure 6A:
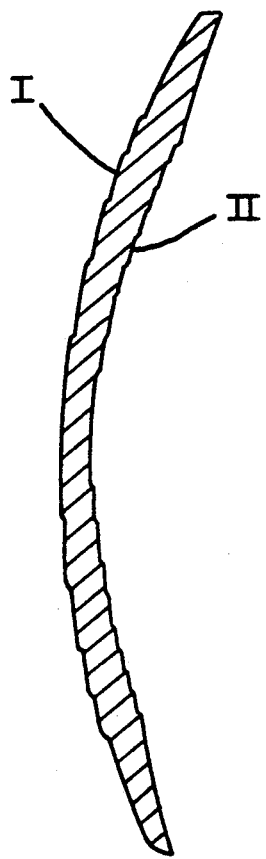
FIG. 6a shows a cross-sectional view of still another embodiment of a bifocal diffraction lens according to the invention.

In FIG. 6a we have a cross-sectional view of a contact lens according to the invention with profiled surface I directing light to a single negative order, and profiled surface II directing light to two adjacent positive orders.

Figure 6B:
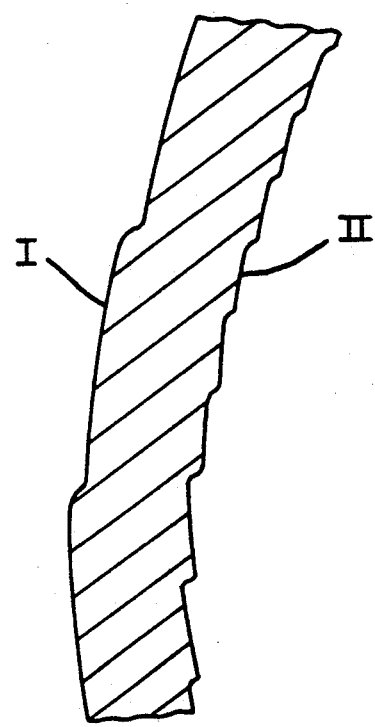

FIG. 6b is a cross-sectional blow-up view of a portion of the contact lens of FIG. 6a.

Figure 7:
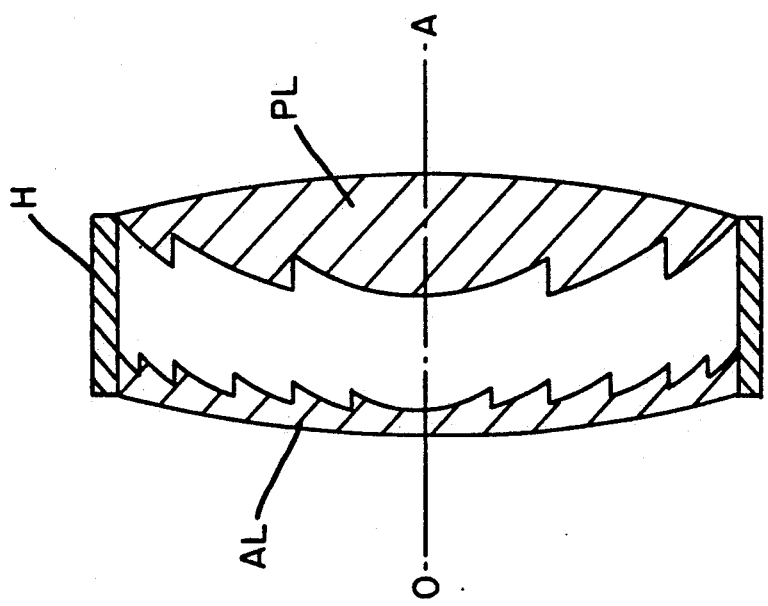
FIG. 7 is a cross-sectional view of a bifocal intraocular lens comprising two distinct lenses according to the invention.

FIG. 7 is a cross-sectional view of a bifocal intraocular lens comprising two distinct lenses according to the invention. The anterior lens AL and posterior lens PL are aligned with a common optical axis O-A, and held in a rigid configuration by the housing H. The anterior lens AL has its posterior surface profiled as a diffractive bifocal while the posterior lens PL has its anterior surface profiled as a diffractive monofocal.

Figure 8:
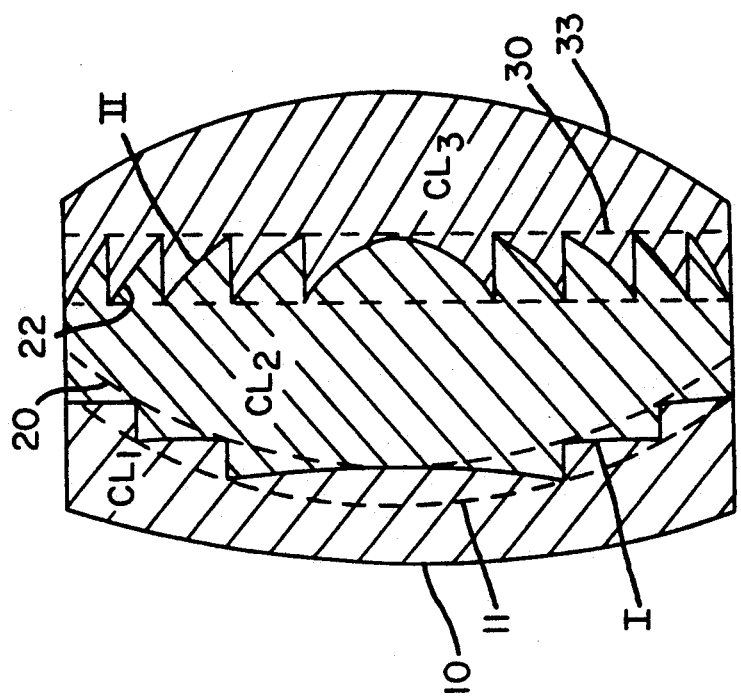
FIG. 8 is a cross-sectional view of a composite material bifocal lens according to the invention.

FIG. 8 is a cross-sectional view of a composite material bifocal lens according to the invention. It comprises three carrier lenses $CL_1$, $CL_2$, and $CL_3$, each comprising a material with a different refractive index. Carrier lens $CL_1$ is bounded by the surfaces 10 and 11, carrier lens $CL_2$ by the surfaces 20 and 22, and carrier lens $CL_3$ by the surfaces 30 and 33. The three media of differing refractive indices are separated by the two diffractive interfaces I and II. Interface I is a diffractive monofocal profile which compensates for some of the chromatic aberration inherent in interface II which is a diffractive bifocal profile.

Figure 11:
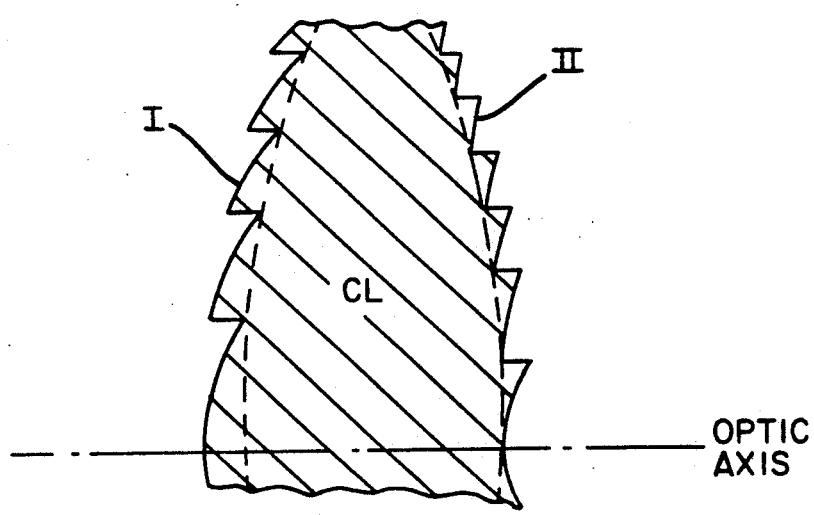
FIG. 11 shows a cross-sectional view of a portion of still another embodiment of a bifocal diffraction lens according to the invention.
Figure 12:
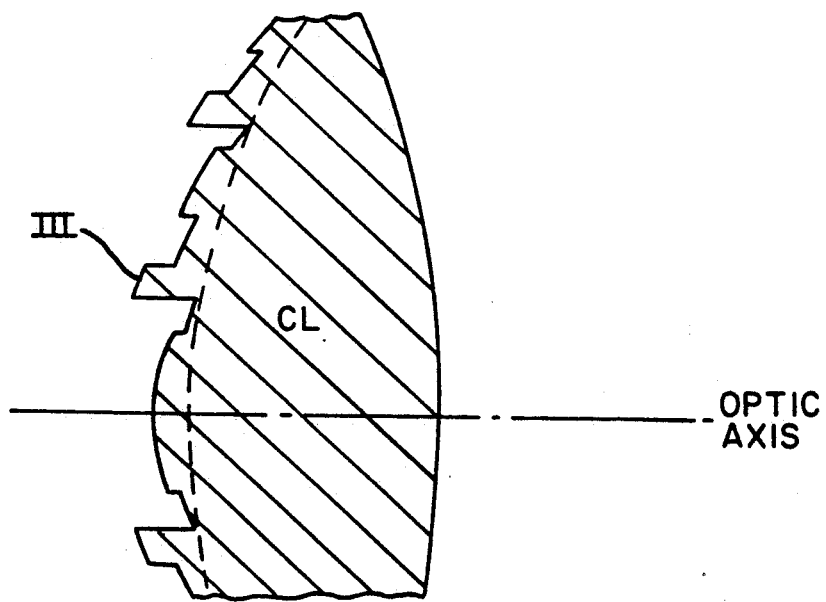
FIG. 12 shows a cross-sectional view of a portion of a bifocal diffraction lens according to the invention, wherein the lens comprises a single diffractive surface.

In FIG. 11 we have a cross-sectional view of a portion of another lens according to the invention. In the embodiment of FIG. 11, surface I determines a +1st order monofocal and surface II determines a 0th/-1st order bifocal. Furthermore, in this embodiment the echelettes of the monofocal and bifocal surfaces I and II are impressed upon a carrier lens CL. Sometimes, as in the case of a contact lens where all the echelettes must contact a single tear layer, it may be more desirable to combine the two separate diffractive surfaces into a single diffractive surface. This is illustrated in FIG. 12 where surfaces I and II have been linearly superimposed to form surface III. While the lenses of FIGS. 11 and 12 are optically equivalent, the lens of FIG. 12 is advantageous for use as a contact lens since it has only one diffractive surface.

Figure 9D:
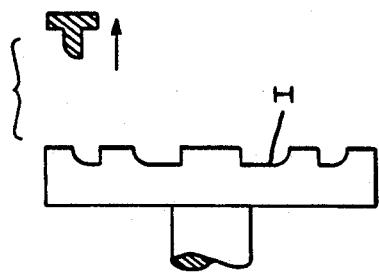
FIG. 9d shows a cross-sectional view of the master blank with its surface fully profiled.
Figure 9C:
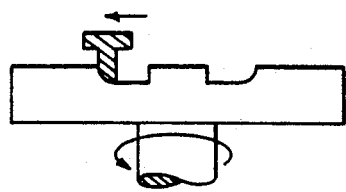
FIG. 9c shows a cross-sectional view of the master blank in the process of being profiled by the cutting tool.
Figure 9B:
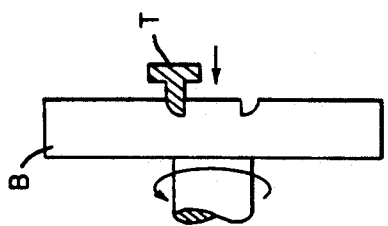
FIG. 9b shows a cross-sectional view of the master blank rotating with the spindle, and the diamond cutting tool plunged into its surface.
Figure 9:
FIG. 9 shows a cross-sectional view of a prior art +1st/−1st order bifocal diffraction lens.
Figure 9A:
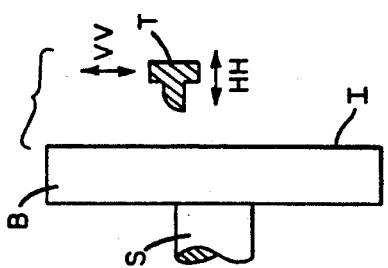
FIG. 9a shows a cross-sectional view of a master blank mounted on a spindle, and a diamond cutting tool.

FIG. 9 is a cross-sectional view of a prior art bifocal that diffracts light to the +1st and −1st orders. In FIG. 9a we see a master blank B, mounted on spindle S, preparatory to having the diffractive profile of FIG. 9 cut into its front surface I. Also shown is a typical tool T that is used in single point diamond turning to cut such a lens. The tool is free to move along axes HH and VV. In FIG. 9b we see the spindle S rotating with the tool T plunged into the blank B. FIG. 9c illustrates the cutting process in progress, and FIG. 9d shows the blank with its finished surface.

Figure 10:
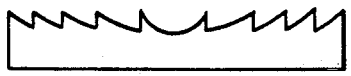
FIG. 10 shows a cross-sectional view of a bifocal diffraction lens according to the invention, which has the same split of chromatic aberration between its images as does the lens of FIG. 9.

It can be seen that the profile of surface I in FIG. 9d does not precisely match the diffractive profile of FIG. 9. This is because a diamond cutting tool will typically have only one knife edge. However, the profiles of this invention, as illustrated in FIG. 10, will not suffer this problem.

I claim:

1. An optical lens comprising;
   (a) a first profiled surface or interface, for diffracting light to two adjacent non negative focal orders m and $(m+1)$, $m=0, 1, 2, \ldots$, comprising a plurality of annular concentric zones spaced according to the formula $r_k = \sqrt{(k\, d\lambda)}\ k=1, 2, 3,$ where $\lambda$ is the design wavelength, d is the primary focal length of the surface or interface. k is a zone, and $r_k$ is the zone radius, and
   (b) a second profiled surface or interface, for diffracting light to a negative focal order $-M$, $M=1, 2, 3, \ldots$, comprising a plurality of annular concentric zones spaced according to the formula $R_k = \sqrt{(kD\lambda)}\ k=1, 2, 3,$ where D is the primary focal length of the surface or interface, and $R_k$ is the zone radius,
said surfaces aligned such that their optical axes are coincident, and such that $(m+1)/d > M/D > m/d$ thereby providing for positive chromatic aberration to be associated with a first focal point and negative chromatic aberration to be associated with a second focal point.

2. An optical lens according to claim 1 wherein;

$(m+\frac{1}{2})/d > M/D > m/d,$ thereby providing that the amount of positive chromatic aberration associated with the first focal point exceeds the amount of the negative chromatic aberration associated with the second focal point.

3. The lens according to claim 2, wherein the lens is configured as a contact lens to be worn on an individual's eye.

4. The lens according to claim 2, wherein the lens is configured as an intraocular lens to be inserted into an individual's eye.

5. An optical lens according to claim 1 wherein;

$(m+1)/d > M/D > (m+\frac{1}{2})/d,$ thereby providing that the amount of negative chromatic aberration associated with the second focal point exceeds the amount of the positive chromatic aberration associated with the first focal point.

6. The lens according to claim 5, wherein the lens is configured as a contact lens to be worn on an individual's eye.

7. The lens according to claim 5, wherein the lens is configured as an intraocular lens to be inserted into an individual's eye.

8. The lens according to claim 1, wherein the lens is configured as a contact lens to be worn on an individual's eye.

9. The lens according to claim 1, wherein the lens is configured as an intraocular lens to be inserted into an individual's eye.

10. An optical lens comprising;
    (a) a first profiled surface or interface, for diffracting light to two adjacent non positive focal orders $-m$ and $-(m+1)$, $m=0,1,2,\ldots$, comprising a plurality of annular concentric zones spaced according to the formula $r_k = \sqrt{(kd\lambda)}\ k=1, 2, 3, \ldots,$ where $\lambda$ is the design wavelength, d is the primary focal length of the surface or interface, k is a zone, and $r_k$ is the zone radius, and
    (b) a second profiled surface or interface, for diffracting light to a positive focal order $+M$, $M=1, 2, 3, \ldots$, comprising a plurality of annular concentric zones spaced according to the formula $R_k = \sqrt{(kD\lambda)}\ k=1, 2, 3, \ldots,$ where D is the primary focal length of the surface or interface, and $R_k$ is the zone radius,
said surfaces aligned such that their optical axes are coincident, and such that $(m+1)/d > M/D > m/d$ thereby providing for positive chromatic aberration to be associated with a first focal point and negative chromatic aberration to be associated with a second focal point.

11. An optical lens according to claim 10 wherein;

$(m+\frac{1}{2})/d > M/D > m/d,$ thereby providing that the amount of negative chromatic aberration associated with the second focal point exceeds the amount of the positive chromatic aberration associated with the first focal point.

12. The lens according to claim 11 wherein the lens is configured as a contact lens to be worn on an individual's eye.

13. The lens according to claim 11 wherein the lens is configured as an intraocular lens to be inserted into an individual's eye.

14. An optical lens according to claim 10 wherein;

$$(m+1)/d > M/D > (m+\tfrac{1}{2})/d,$$

thereby providing that the amount of positive chromatic aberration associated with the first focal point exceeds the amount of the negative chromatic aberration associated with the second focal point.

15. The lens according to claim 14 wherein the lens is configured as a contact lens to be worn on an individual's eye.

16. The lens according to claim 14 wherein the lens is configured as an intraocular lens to be inserted into an individual's eye.

17. The lens according to claim 10 wherein the lens is configured as a contact lens to be worn on an individual's eye.

18. The lens according to claim 10 wherein the lens is configured as an intraocular lens to be inserted into an individual's eye.

19. An optical lens comprising one profiled surface or interface, for diffracting light to two distinct focal powers, comprising a plurality of annular concentric zones, and providing for positive chromatic aberration to be associated with a first focal point and negative chromatic aberration to be associated with a second focal point such that the amount of negative chromatic aberration exceeds the amount of positive chromatic aberration.

20. The lens according to claim 19, wherein the lens is configured as a contact lens to be worn on an individual's eye.

21. The lens according to claim 19, wherein the lens is configured as an intraocular lens to be inserted into an individual's eye.

22. An optical lens comprising one profiled surface or interface, for diffracting light to two distinct focal powers, comprising a plurality of annular concentric zones, and providing for positive chromatic aberration to be associated with a first focal point and negative chromatic aberration to be associated with a second focal point such that the amount of positive chromatic aberration exceeds the amount of negative chromatic aberration.

23. The lens according to claim 22, wherein the lens is configured as a contact lens to be worn on an individual's eye.

24. The lens according to claim 22, wherein the lens is configured as an intraocular lens to be inserted into an individual's eye.

* * * * *